United States Patent [19]
Jones

[11] Patent Number: 6,102,875
[45] Date of Patent: *Aug. 15, 2000

[54] APPARATUS FOR COMBINED APPLICATION OF MASSAGE, ACCUPRESSURE AND BIOMAGNETIC THERAPY

[76] Inventor: Rick E. Jones, 5654 Montclair Cir., Rocklin, Calif. 95677

[ * ] Notice: This patent issued on a continued prosecution application filed under 37 CFR 1.53(d), and is subject to the twenty year patent term provisions of 35 U.S.C. 154(a)(2).

[21] Appl. No.: 08/784,352
[22] Filed: Jan. 16, 1997
[51] Int. Cl.$^7$ .................................................. A61H 15/00
[52] U.S. Cl. .......................... 601/113; 601/112; 601/131; 601/15; 601/18; 601/19
[58] Field of Search .................................. 601/15, 18, 19, 601/20, 112, 113, 128, 129, 130, 131

[56] References Cited

U.S. PATENT DOCUMENTS

| | | |
|---|---|---|
| D. 329,291 | 9/1992 | Wollman . |
| D. 329,292 | 9/1992 | Wollman . |
| D. 330,256 | 10/1992 | Wollman . |
| D. 331,467 | 12/1992 | Wollman . |
| D. 342,138 | 12/1993 | Wollman et al. . |
| D. 342,139 | 12/1993 | Wollman et al. . |
| D. 350,396 | 9/1994 | Wollman et al. . |
| D. 360,695 | 7/1995 | Wollman . |
| 1,064,093 | 6/1913 | Schulze . |
| 1,557,417 | 10/1925 | Cheney . |
| 1,899,208 | 2/1933 | Murphy . |
| 2,034,758 | 3/1936 | Hicke, Jr. ................................. 601/113 |
| 2,043,114 | 6/1936 | Ruttger-Pelli . |
| 2,258,931 | 10/1941 | Heer et al. . |
| 3,077,878 | 2/1963 | Baulard-Cogan . |
| 3,095,874 | 7/1963 | Frajdenrajch . |
| 3,878,837 | 4/1975 | Werding . |
| 4,178,921 | 12/1979 | Kosiak . |
| 5,323,499 | 6/1994 | Chan . |
| 5,429,585 | 7/1995 | Liang ........................................ 601/57 |
| 5,437,607 | 8/1995 | Taylor . |
| 5,632,720 | 5/1997 | Kleitz ...................................... 601/15 |
| 5,725,483 | 3/1998 | Podolsky .................................. 601/15 |

FOREIGN PATENT DOCUMENTS

| | | |
|---|---|---|
| 2306-677 | 11/1976 | France . |
| 405293145 | 11/1993 | Japan ..................................... 601/112 |
| 313679 | 6/1956 | Switzerland . |
| 877548 | 9/1961 | United Kingdom . |

Primary Examiner—Danton D. DeMille
Assistant Examiner—Benjamin Koo
Attorney, Agent, or Firm—John P. O'Banion

[57] ABSTRACT

A handheld apparatus for simultaneously applying massage, accupressure and biomagnetic therapy to an area of the human body in which an electric motor rotates a carrier that guides several metal balls in a circular motion to produce a kneading effect and magnetic force is applied to the point of contact through the balls. The balls rotate to provide superior physical stimulation with minimal resistance and the magnetic force promotes healing by removing toxins and waste products in the treated area and replenishing the treated area with oxygen-rich blood and nutrients. In addition, vibrational motion can be imparted to the balls.

7 Claims, 3 Drawing Sheets

APPARATUS FOR COMBINED APPLICATION OF MASSAGE, ACCUPRESSURE AND BIOMAGNETIC THERAPY

BACKGROUND OF THE INVENTION

1. Field of the Invention

This invention pertains generally to handheld massage devices, and more particularly to a handheld apparatus that simultaneously provides massage, accupressure and biomagnetic therapy to an area of the body.

2. Description of the Background Art

It is well known that massage therapy can be a beneficial form of treatment for sore muscles and the like, and that pressure applied in combination with motion over a treatment area is a generally recognized form of treatment for stiffness, fatigue, soreness, muscle strains and/or disorders that can have detrimental effects on an athlete's progress in training and conditioning programs. This is particularly evident in sports where the intent of training is to facilitate peak performance, such as track and field, gymnastics, swimming, wrestling, skating, and weight lifting and, to some extent, basketball, baseball and football.

The specific type of massage therapy used must be adaptable and sensitive to the specific demands of each sport, the condition of the athlete, and the period of training when specific therapies are contraindicated, as well as provide a means to assist the body's natural healing process. Lost practice time due to muscular disorders, especially when training volume is relatively low and intensity is high, can have serious consequences. Nevertheless, an athlete's ability to adhere to prudent therapies, or more importantly, to maintain rehabilitative progression, is essential to achieving peak performance.

Massage therapy can be applied in a number of ways, ranging from manual treatment by a masseuse to use of a mechanical device to ease the application of pressure and motion. A number of mechanical devices have been previously developed in response to a general desire to ease the massage therapy process. For example, U.S. Pat. No. 1,557,17 issued to Cheney on Oct. 13, 1925, U.S. Pat. No. 1,899,208 issued to Murphy on Feb. 28, 1933, U.S. Pat. No. 2,034,758 issued to Hicke, Jr. on Mar. 24, 1936, U.S. Pat. No. 2,043,114 issued to Ruttger-Pelli on Jun. 2, 1936, U.S. Pat. No. 2,258,931 issued to Heer et al. in Oct. 14, 1941, and U.S. Pat. No. 3,077,878 issued to Baulard-Cogan on Feb. 19, 1933, all describe handheld massage machines that use an electric motor or other means to rotate an applicator containing multiple rotating balls. U.S. Pat. No. 3,878,837 issued to Werding on Apr. 22, 1975, shows a handheld massaging apparatus in which a motor rotates multiple rollers.

It is also known that magnets can be used as an effective adjunct in the treatment of acute and chronic pain disorders. Magnets can facilitate the healing of soft tissue, bones and joints. The basis of "biomagnetic therapy" is to increase the flow of blood and oxygen to areas in the body that are injured and/or under distress. Swiss Pat. No. 313679 published on Apr. 30, 1956, shows a handheld massage therapy device having a rotating carrier containing multiple magnetic balls.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present invention pertains to an apparatus for simultaneously applying massage, accupressure and biomagnetic therapy to an area of the human body. By combining the benefits of massage, accupressure and biomagnetic therapy, the present invention helps stimulate the body's natural electromagnetic energy. For example, the human body contains about 4 to 5 grams of iron which is present in hemoglobin. Hemoglobin contains positive and negative ions and, when a magnetic field is applied to an area on the body, magnetic waves pass through the soft tissues and secondary currents are induced. When muscle tissue is damaged, the area immediately emits a positive magnetic charge. This positive charge may stagnate the natural flow of blood and oxygen. By applying an external magnetic field to the affected tissue, the ionic movement of hemoglobin is accelerated and the body's neural receptors are augmented.

By way of example and not of limitation, the present invention comprises a housing containing an electric motor, a shaft coupled to the electric motor, a disc coupled to the shaft, a plurality of metal balls positioned in peripheral apertures in the disc, and a magnet positioned between the motor and the disc and adjacent to the balls. The motor causes the disc to rotate about the axis of the shaft, so that the balls move with a circular motion. In addition, the balls are held in place by the magnet, which allows them to freely rotate about their own axes. At the same time, magnetic force from the magnet is transferred through the metal balls and into the soft tissues of the body. As the disc rotates, the balls freely rotate over the soft tissues in a gentle circular motion. The action of the balls creates a "kneading" effect over the soft tissues of the muscle minimizing resistance created by rolling over the muscle. The rotating motion of the invention combined with the application of magnetic force helps eliminate the toxins and waste products and helps replenish the area with oxygen-rich blood and nutrients.

An object of the invention is to provide an apparatus for applying combined massage, accupressure and biomagnetic therapy to an area of the body.

Another object of the invention is to provide an apparatus that will enhance the healing process and assist in minimizing rehabilitation time.

Another object of the invention is to provide an apparatus that will "knead" the soft tissues of the muscle.

Another object of the invention is to provide for application of magnetic force to eliminate toxins and waste products in the body.

Another object of the invention is to provide an apparatus that will replenish a treated area with oxygen-rich blood and nutrients.

Another object of the invention is to increase overall blood circulation in a treated area.

Another object of the invention is to enhance the natural healing process in the body.

Another object of the invention is to ease pain.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
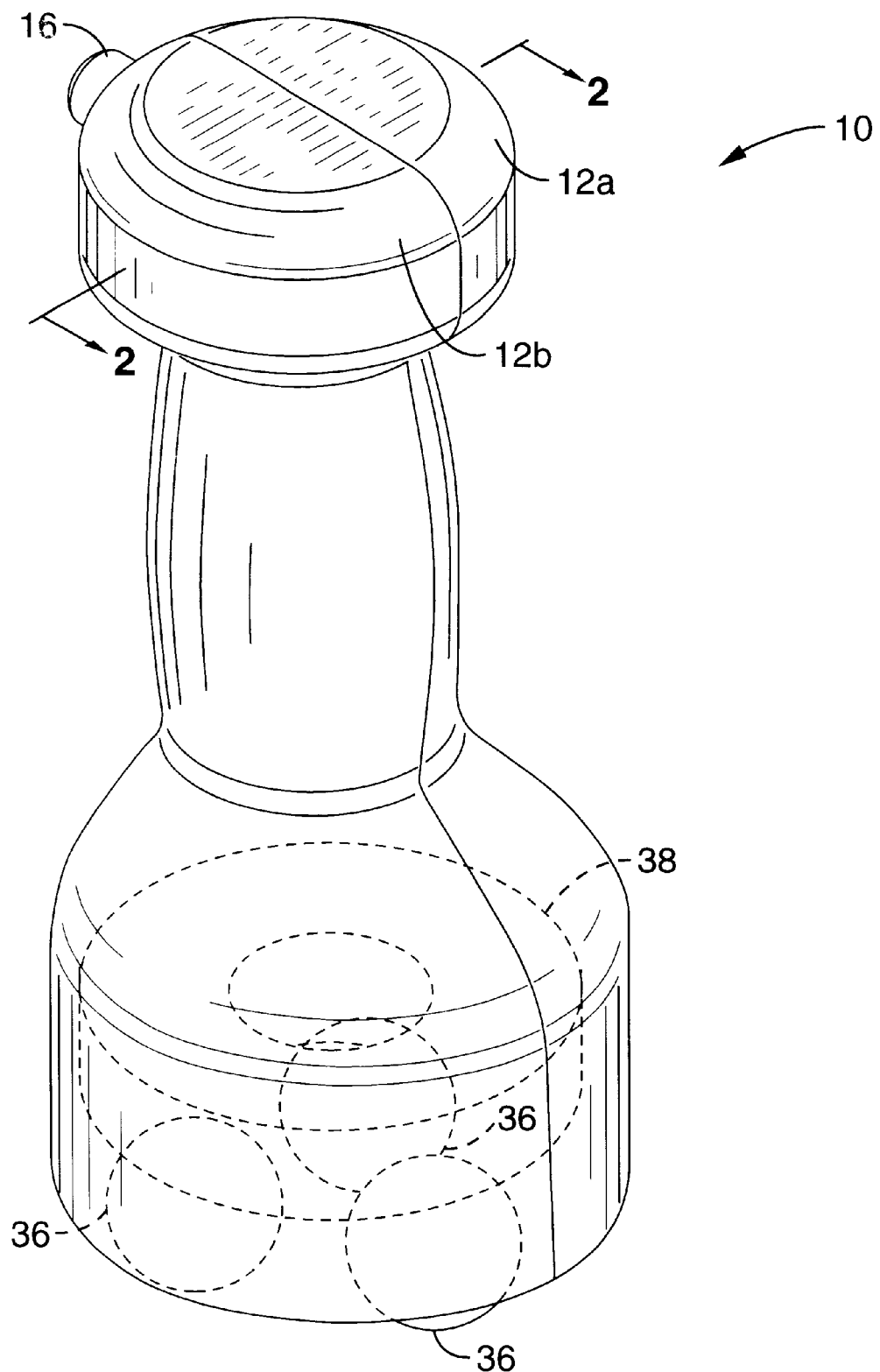
FIG. 1 is a perspective view of a handheld accupressure and biomagnetic therapy apparatus in accordance with the present invention.
Figure 2:
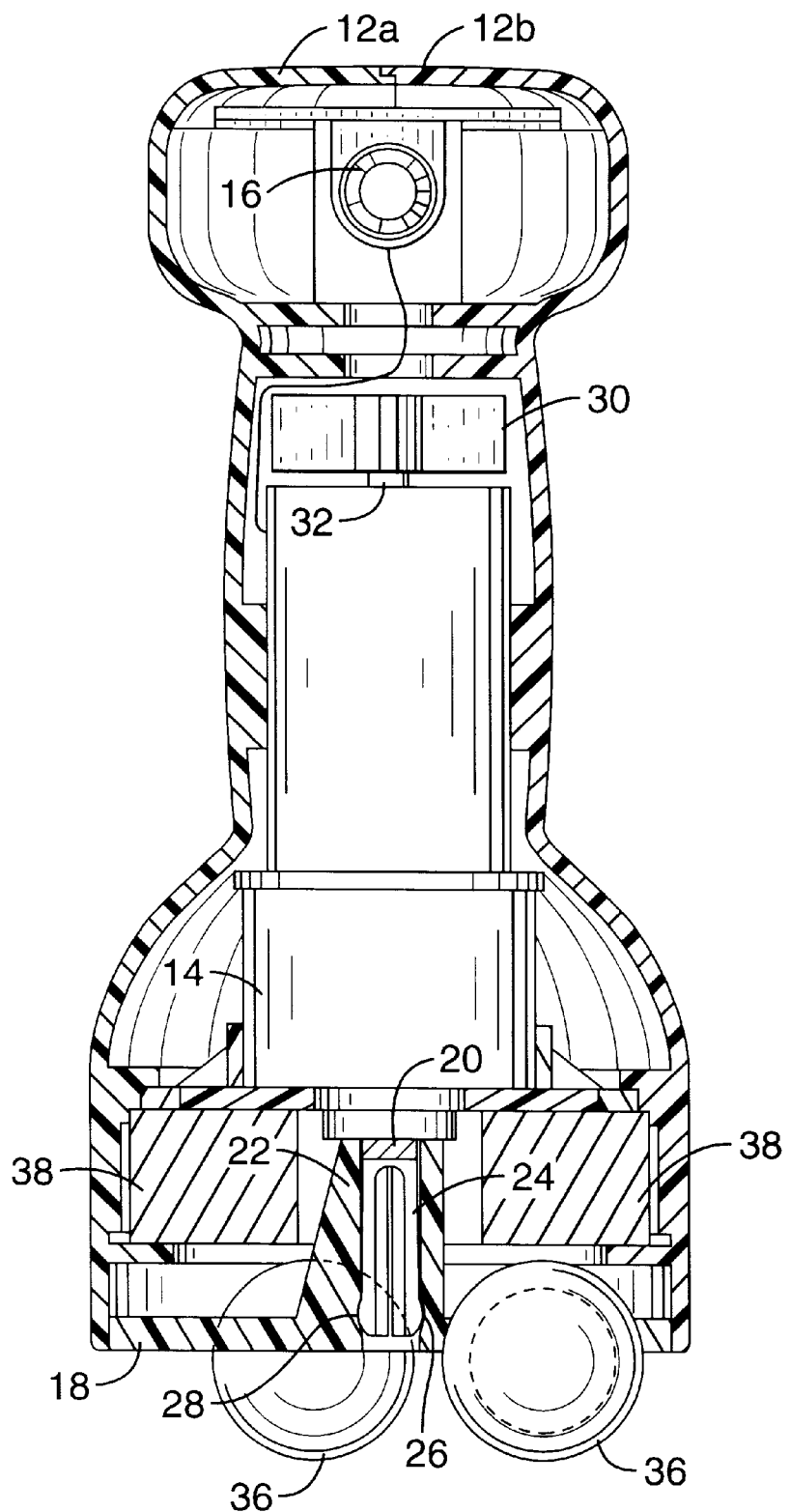
FIG. 2 is cross-sectional view of the apparatus shown in FIG. 1 taken through line 2—2.
Figure 3:
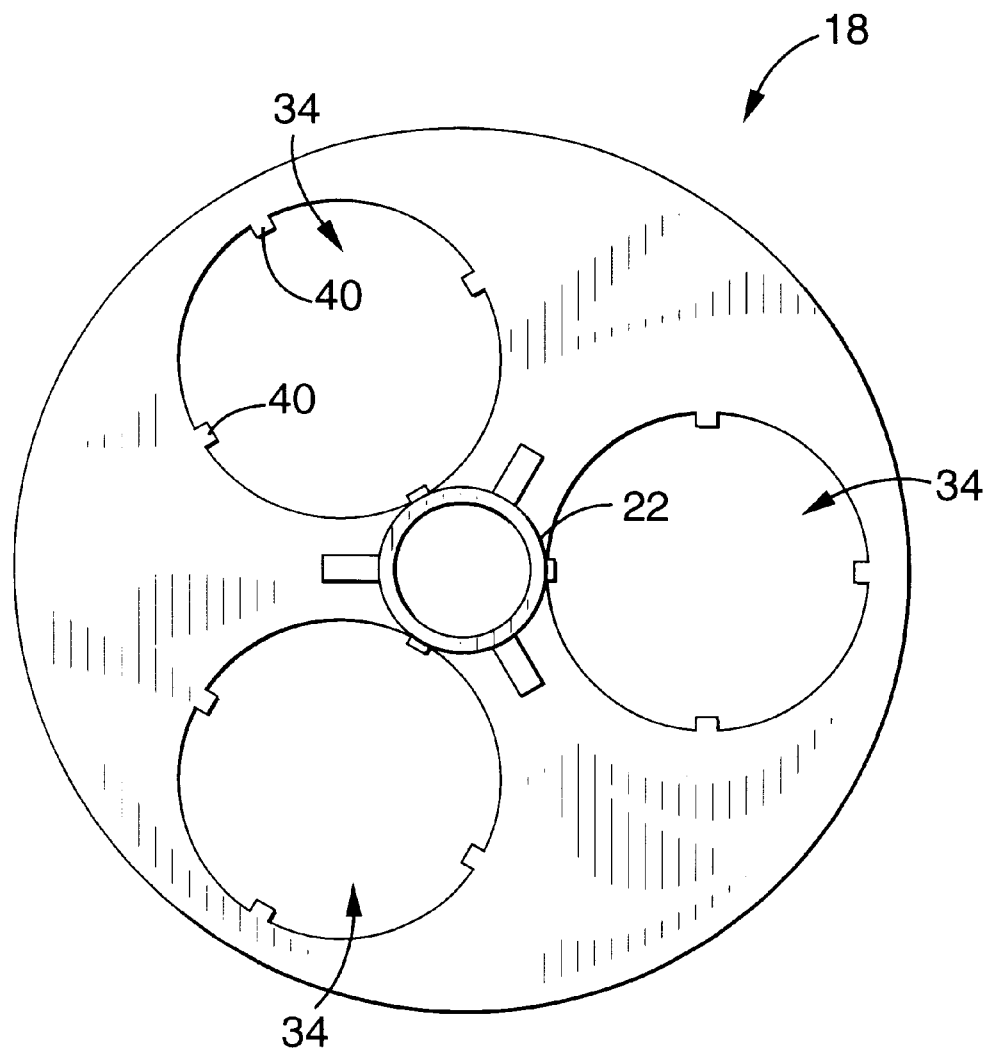
FIG. 3 is a top plan view of the rotor portion of the apparatus shown in FIG. 1 and FIG. 2.

Referring more specifically to the drawings, for illustrative purposes the present invention is embodied in the apparatus generally shown in FIG. 1 through FIG. 3, where like reference numbers denote like parts. It will be appreciated that the apparatus may vary as to configuration and as to details of the parts without departing from the basic concepts as disclosed herein.

Referring first to FIG. 1 and FIG. 2, a handheld accupressure and biomagnetic therapy apparatus 10 in accordance with the present invention is generally shown. The apparatus comprises a split housing 12a, 12b, containing an electric motor 14 which is preferably of a variable speed type. The speed of motor 14 set by a combination "on/off" switch and speed control 16 using a conventional electronic speed control or the like (not shown). Alternatively, motor 14 can operate at a fixed speed using direct drive or motor 14 can be of a high speed type that is geared down through a conventional gear reduction arrangement. Motor 14 could also be of a reversible type and a direction reversing switch could be provided therewith. Power for motor 14 can be provided by internal batteries (not shown) or an external power supply coupled to motor 14 by a power cable (not shown) in any conventional manner.

A disc-shaped rotor 18 is coupled to motor 14 using a shaft 20 such that rotor 18 will rotate about the axis of shaft 20 when motor 14 is operational. The rotational speed of rotor 18 is preferably variable between approximately 25 to 75 rpm, which is determined by the speed of electric motor 14. Preferably, rotor 18 includes a central collar 22 which is coupled to shaft 20 by means of an intermediate sleeve 24 that is pressed onto shaft 20. Sleeve 24 is typically has a flared circumferential end 26 that engages an annular detent 28 in collar 22. In this way, rotor 18 can be removed from shaft 20 by separating collar 22 from sleeve 24 with a longitudinal pulling motion. Once removed, rotor 18 can be cleaned, sterilized or replaced. Alternatively, collar 22 can be coupled to shaft 20 using one or more set screws (not shown) or other conventional coupling means. In addition, a fan 30 can be coupled to a shaft 32 extending from the opposite end of motor 14 for cooling purposes.

Referring also to FIG. 3, rotor 18 has a plurality of peripherally spaced apertures 34 in which metal balls 36 are placed. Preferably, there are three apertures 34 and three balls 36 arranged in a triangular fashion as shown so as to provide a "kneading" motion during rotation. It will be appreciated that kneading motion can also be produced with fewer balls, but with a longer time between repeat contact with an area. Conversely, additional balls will decrease the time between repeat contact.

While balls 36 could be held in rotor 18 in a variety of conventional ways, they are preferably held in place using one or more magnets 38 positioned between motor 14 and rotor 18 and adjacent to balls 36. Magnet 38 is preferably annular in shape to match the shape of rotor 16 with shaft 20 and collar 22 extending through the center thereof. Alternatively, magnet 38 can be a plurality of magnets or magnet segments placed around the periphery of housing 12a, 12b. Apertures 34 in rotor 18 typically have a diameter approximately matching that of balls 36. In order to reduce friction as balls 36 rotate, each aperture 34 includes a plurality of spacer tabs 40 that hold balls 36 out from the inner edge of the apertures as well as away from magnet 38. In this way, balls 36 will not touch magnet 38 or the inner edge of apertures 34. Instead, the only point of contact will be with tabs 40. By making balls 36 steel, iron or the like, they will be held in place by magnet 38 and freely rotate about their own central axes CA when rotor 18 rotates and pressure is being applied to an object such as a person undergoing therapy. And, since balls 36 are made from steel or like magnetic material, magnetic force from magnet 38 will be transferred through balls 36 and to tissue contacting balls 36 during use of the apparatus.

Magnet 38 is typically a 1000 Gauss magnet, which is provide for approximately 480 Gauss to be present at the point of contact between the balls and the tissue. This will provide a safe and therapeutic modality. However, the apparatus is not recommended for persons with pacemakers, especially those with attached defibrillators, or pregnant women. A field as low as 10 Gauss can affect pacemaker operation.

It will be appreciated that, instead of using magnet 38 to hold supply the magnetic energy, balls 36 could themselves be made from a magnetic or magnetized material. However, to do so would require a complicated race or carrier to hold them in place with rotor 18 in a way which will allow the balls to freely rotate in any direction about their central axes. Additionally, the amount of magnetic force applied could not be easily varied where the balls themselves are magnetic. In contrast, magnet 38 could be replaced with a stronger or weaker magnet to change the magnetic field without having to replace balls 36.

It will also be appreciated that balls 36 could be replaced with cylindrical rollers arranged around the periphery of rotor 18. Also, balls 36 could be made oblong or another non-spherical shape if desired. However, spherical balls are preferred because they can rotate in any direction about their central axes CA, whereas cylindrical rollers would rotate only about their longitudinal axes and oblong balls would rotate with a non-uniform motion.

While the present invention applies accupressure using rotating balls, physical stimulation could also be applied by substituting a conventional electromechanical or electromagnetic vibrator for motor 14. A backing plate or the like (not shown) could be coupled to collar 22 and positioned in contact with balls 36 between the balls and magnet 38. Reciprocating motion or the like would then be imparted to collar 22 and backing plate, and transmitted to balls 36. Balls 36 would then "bounce" over the area of the body being treated. Balls 36 still could be held in place with magnet 38 or be made of a magnetic material themselves to provide for simultaneous application of biomagnetic therapy. If the vibrator is of a conventional electromagnetic type, the magnetic force from the vibrator may also be sufficient to replace magnet 38. And, although the superior "kneading" effect of rotating balls would not result, the physical stimulation would be sufficient to provide therapeutic benefits. It is also contemplated that vibration and rotational motion of balls 36 could be combined. The construction of motor driven handheld vibrators is well known in the art and, therefore, is not described in detail herein.

Accordingly, the present invention is a novel massage product that will enhance the healing process and assist in minimizing rehabilitation time. The apparatus allows a therapist or even the individual themselves to apply gentle massaging pressure directly to the muscle. The magnet holding the balls in place allow the balls to freely rotate over the muscle in a circular motion. This action creates a kneading effect over the soft tissues of the muscle minimizing the resistance created by rolling over the muscle. The rotating motion of the apparatus combined with application of magnetic force helps to eliminate toxins and waste products and replenish the area with oxygen-rich blood and nutrients. The increased concentrations of ions in the hemoglobin stimulate the autonomic nervous system to dilate the capillaries, resulting in increased overall circulation, and providing for the effective removal of waste products. The muscle's natural healing process is thereby enhanced, which further bolsters the area's resistance to degenerative effects. In addition to increasing the flow of blood to the soft tissues and bones, the ion concentrations across the nerve axons may increase the axon resting membrane potential. The natural energy balance of sodium (Na+), potassium (K+) and chloride (Cl−) located along the axon membranes are augmented and when a "pain" stimulus is received, the impulse is not intense enough to depolarize and transmit a signal. Once the axon's resting membrane potential drops from 70 mV to 55 mV (i.e., threshold potential), a pain stimulus is sent to the brain. In theory, chronic pain is a result of a decreased resting potential (i.e., 60 mV), thus only a small change (−5 mV) is needed to produce pain. More importantly, pain results in an impulse which may decrease performance and/or training quality. In the present invention, the magnetic field passes through in a direction perpendicular to the ionic movement of the axon which produces a voltage. This voltage may add to the nerve's resting potential and raise its threshold, making it less likely to depolarize. Also, the deflecting action of the magnetic filed of the ions could potentially make it more difficult for the ions to pass through the nerve membrane. The entire excitation of pain is thus influenced and the subjective perception of pain changed. The present invention will both ease pain and increase circulation, and invigorate muscles so that the athlete can recover from injury more quickly and without a significant loss in performance.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for applying massage, accupressure and biomagnetic therapy to a subject, comprising:
   (a) a handheld housing having a proximal end and a distal end;
   (b) a rotor carried by said housing at said distal end of said housing, said rotor having a plurality of peripheral apertures, each said aperture having an inner edges with a plurality of spaced-apart tabs disposed along said inner edge;
   (c) a plurality of metallic balls, each said ball carried by a corresponding aperture in said rotor, each said ball having a central axis, each said ball being rotatable within its corresponding aperture in any direction about its central axis; and
   (d) a magnet carried by said housing and positioned between said electric motor and said rotor;
   (e) wherein said balls are held in place in said rotor by magnetic force exerted by said magnet on said balls, wherein said tabs hold said balls away from said magnet and prevent said balls from contacting said magnet, wherein said tabs hold said balls away from said inner surfaces of said apertures and prevent said balls from contacting said inner surfaces of said apertures, and wherein said balls are removable from said rotor by moving said balls distal of said rotor and breaking said magnetic force exerted on said balls by said magnet.

2. An apparatus as recited in claim 1, further comprising:
   (a) an electric motor positioned within said housing; and
   (b) a rotating shaft coupling said electric motor to rotor.

3. An apparatus as recited in claim 2, wherein magnetic energy is capable of being transferred from said magnet, through said balls, and to an object in contact with said balls.

4. An apparatus as recited in claim 1, further comprising vibrator means for imparting vibrational motion to at least one of said balls.

5. An apparatus for applying massage, accupressure and biomagnetic therapy to a subject, comprising:
   (a) a housing having a proximal end and a distal end;
   (b) an electric motor positioned within said housing;
   (c) a shaft coupled to said electric motor;
   (d) a rotor coupled to said shaft and positioned at said distal end of said housing, said rotor having a plurality of peripheral apertures, each said aperture having an inner edge with a plurality of spaced-apart tabs disposed along said inner edge;
   (e) a plurality of metal balls, each said metal ball positioned within a corresponding one of said apertures in said rotor, each said ball having a central axis, each said ball rotatable in any direction about its central axis upon contact with an object and upon rotation of said rotor; and
   (f) a magnet disposed between said electric motor and said rotor;
   (g) wherein said balls are held in place in said rotor by magnetic force exerted by said magnet on said balls, wherein said tabs hold said balls away from said magnet and prevent said balls from contacting said magnet, wherein said tabs hold said balls away from said inner surfaces of said apertures and prevent said balls from contacting said inner surfaces of said apertures, and wherein said balls are removable from said rotor by moving said balls distal of said rotor and breaking said magnetic force exerted on said balls by said magnet.

6. An apparatus as recited in claim 5, wherein magnetic force is capable of being transferred from said magnet, through said balls, to an object in contact with said balls.

7. An apparatus for applying massage, accupressure and biomagnetic therapy to a subject, comprising:
   (a) a housing having a proximal end and a distal end;
   (b) an electric motor positioned within said housing;
   (c) a rotating shaft coupled to said electric motor;
   (d) a rotating disc coupled to said shaft and positioned at said distal end of said housing, said disc having a plurality of peripheral apertures, each said aperture having an inner edge with a plurality of spaced-apart tabs disposed along said inner edge;
   (e) a magnet disposed between said electric motor and said rotating disc; and (f) a metal ball positioned in each said aperture, each said ball having a central axis;

(g) wherein said balls are held in place in said disc by magnetic force exerted on said balls by said magnet, wherein said tabs hold said balls away from said magnet and prevent said balls from contacting said magnet, wherein said tabs hold said balls away from said inner surfaces of said apertures and prevent said balls from contacting said inner surfaces of said apertures, wherein said balls are removable from said rotor by moving said balls distal of said rotor and breaking said magnetic force exerted on said balls by said magnet, wherein each said ball rotates within a corresponding aperture in any direction about the central axis of said ball when said disc rotates and said ball contacts an object, wherein said magnet holds said balls within their corresponding aperture in said rotor, and wherein magnetic force is capable of being transferred from said magnet, through said balls, and to an object in contact with said balls.

* * * * *